United States Patent [19]

van den Brink et al.

[11] 4,096,170

[45] Jun. 20, 1978

[54] PREPARATION OF ESTERS

[75] Inventors: Marinus J. van den Brink; Roger A. Sheldon, both of Amsterdam, Netherlands

[73] Assignee: Shell Oil Company, Houston, Tex.

[21] Appl. No.: 796,260

[22] Filed: May 12, 1977

[30] Foreign Application Priority Data

Jul. 26, 1976  United Kingdom ............... 31047/76

[51] Int. Cl.² ................ C07C 120/00; C07C 121/46; C07C 121/48
[52] U.S. Cl. ......................... 260/465 D; 260/287 D; 260/287 N; 260/294.9; 260/326.13 R; 260/326.2; 260/332.2 R; 260/347.4; 260/464; 544/336; 544/335
[58] Field of Search ........................... 260/465 D, 464

[56] References Cited

U.S. PATENT DOCUMENTS 3,835,176   9/1974   Matsuo et al. ................... 260/465 D
4,000,180   12/1976  Punja ..................................... 260/464

OTHER PUBLICATIONS

Conia et al., Bulletin Soc. Chim. France (1963), pp. 755–763.

*Primary Examiner*—Joseph Paul Brust

[57] ABSTRACT

Certain cyclopropanecarboxylic acid esters also containing a cyano group are prepared by reacting an aldehyde, a salt of hydrocyanic acid and a 2-halocyclobutanone in an aprotic solvent.

13 Claims, No Drawings

PREPARATION OF ESTERS

BACKGROUND OF THE INVENTION

I. Field of the Invention

The invention relates to a process for the preparation of certain cyano-substituted cyclopropanecarboxylic acid esters by reacting an aldehyde, a salt of hydrocyanic acid and a 2-halocyclobutanone.

II. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, affords the desired esters. The cyclopropanecarboxylic acids can be prepared and converted in a known manner to the corresponding cyclopropanecarbonyl halides.

Such a process has the disadvantages that the cyclopropanecarboxylic acids and their carbonyl halides must be prepared in separate stages.

The present invention obviates this disadvantage.

SUMMARY OF THE INVENTION

The present invention is directed to a process for the preparation of an ester of formula I

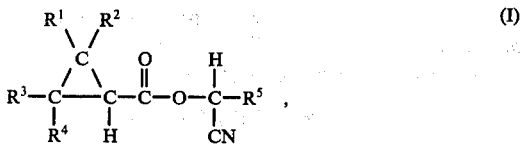     (I)

wherein $R^1$, $R^2$, $R^3$, $R^4$ and $R^5$ each represents a substituted or unsubstituted hydrocarbyl group or a hydrogen atom, which comprises contacting
(a) an aldehyde of formula II

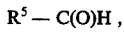     (II)

wherrein $R^5$ has the same meaning as in formula I,
(b) a salt of hydrocyanic acid,
(c) a 2-halocyclobutanone of formula III

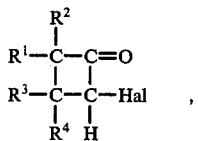     (III)

wherein $R^1$, $R^2$, $R^3$ and $R^4$ have the same meaning as in formula I and Hal represents a halogen atom having an atom number of from 9 to 53, inclusive, and
(d) one or more aprotic solvents.

The present invention enables a three-step process comprising ring contrction of the 2-halocyclobutanone of formula III to a cyclopropanecarboxylic acid, conversion of this acid into its carbonyl halide and reaction of this carbonyl halide with an aldehyde and a cyanide to be replaced by a one-step process.

The aprotic solvent may be substantially water-immiscible or may be water-miscible, i.e., it dissolves less than 5%w or at least 5%w of water, respectively, at the temperature at which the process is carried out. Substantially water-immiscible aprotic solvents are preferably used in the presence of water, because this promotes the formation of the esters of formula I. The formation of these esters is most promoted in solvents comprising one or more alkanes. Examples of suitable alkanes are n-hexane, n-heptane, n-octane, n-nonane, n-decane and their isomers, for example 2-methylpentane, 3-methylpentane, 2-methylhexane, 3-methylhexane and 2,4,4-trimethylpentane. Gasolines rich in alkanes, such as gasolines with a boiling range at atmospheric pressure between, for example, 60° and 80° C are also very suitable. Very good results have been obtained with n-heptane.

Examples of other substantially water-immiscible solvents are cycloalkanes, for example cyclohexane and methylcyclohexane, and aromatic hydrocarbons, such as benzene, toluence, o-, m- and p-xylene and the trimethylbenzes, ethers such as diethyl ether and diisopropyl ether, alkanones, such as diisobutyl ketone and halogenated hydrocarbons, such as carbon tetrachloride.

The (cyclo)alkanes used according to this invention may contain up to 50% by weight of other substantially water-immiscible aprotic solvents, for example, aromatic hydrocarbons such as benzene or toluene or chlorinated hydrocarbons. For example, alkanes and aromatic hydrocarbons, may be used, for instance n-heptane containing about 10%w of benzene and/or toluene.

The amount of water is not critical and may vary within wide limits. On the one hand, it is preferably less than the amount required to obtain a 25%w and particularly 40%w aqueous solution with the starting amount of a water-soluble salt of hydrocyanic acid so as to reduce the possibility of reaction of the 2-halocyclobutanone of formula III with water with formation of cyclopropanecarboxylic acid, and on the other hand, it is preferably sufficiently large to dissolve all of this cyanide at the temperature at which the process is conducted so as to reduce the reaction time. However, the presence of solid water-soluble salt of hydrocyanic acid is not excluded.

The temperature at which the process is suitably conducted is usually above 20° C and is preferably in the range of from 50° C. The esters of formula I are usually obtained in the highest yield in the range of from 60° to 70° C.

Water-miscible aprotic solvents are preferably used in the absence of water. Examples of such solvents are N,N-dimethylformamide, N,N-dimethylacetamide, dimethyl sulphoxide, N-methylpyrrolidone, acetonitrile, tetrahydrothiophene 1,1-dioxide, nitromethane and tetrahydrofuran. Very good results have been obtained with N,N-dimethylformmide.

The salt of hydrocyanic acid is soluble in water when a substantially water-immiscible aprotic solvent is used in the pressure of water and soluble in the aprotic solvent when the aprotic solvent is substantially water-miscible. Examples of suitable salts of hydrocyanic acid are alkali metal cyanides, alkaline earth metal cyanides and tetrahydrocarbylammonium cyanides. Alkali metal cyanides are preferred. Potassium cyanide is particularly preferred, because it affords the esters of formula I in a shorter reaction time and in a higher yield than sodium cyanide.

The molar ratios of the aldehyde of formula II to the 2-halocyclobutanone of formula III and of the salt of hydrocyanic acid to the aldehyde of formula II are not critical and may vary within wide limits. The former molar ratio is preferably equal to one and the latter is preferably in the range of from 1.0 to 1.5 and particularly from 1.1 to 1.3.

The hydrocarbyl groups represented by $R^1$, $R^2$, $R^3$ and $R^4$ in formula III and by $R^5$ in formula may be, for example, an alkyl group containing from 1 to 6 carbon atoms, a cycloalkyl group containing from 3 to 6 carbon atoms, a phenyl group, or an ethylenically unsaturated group containing from 2 to 4 carbon atoms. $R^5$ preferably represents a substituted or unsubstituted aryl group. These aryl groups may be carbocyclic or heterocyclic. Examples of carbocyclic groups are phenyl, 1-naphthyl, 2-naphthyl and 2-anthryl groups. Heterocyclic aromatic groups are derived from hetero-aromatic compounds which, according to Kirk-Othmer, "Encyclopedia of Chemical Technology", Second Edition, Volume 2 (1963), page 702, are defined as being obtained by replacement of one or more carbon atoms of a carbocyclic aromatic compound by a heteroatom, for example pyridine, pyrimidine, pyrazine, quinoline and isoquinoline; the hetero-aromatic compounds include heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable. Examples of substituents are hydrocarbyl, hydrocarbyloxy or halogen groups. Very good results have been obtained with phenoxybenzaldehydes, particularly m-phenoxybenzaldehyde.

$R^1$, $R^2$, $R^3$ and $R^4$ in formula III preferably represent alkyl groups, particularly alkyl groups with one to six carbon atoms. The alkyl groups may be linear or branched. Methyl groups are particularly preferred.

The Hal atom in formula III preferably represents a chlorine or bromine atom, in particular a chlorine atom.

The process according to the invention may be carried out by mixing the total amounts of the starting compounds with vigorous agitation, e.g., stirring. If desired, the aldehyde of formula II, the salt of hydrocyanic acid, the aprotic solvent and water, if any, may be mixed, followed by gradual addition of the cyclobutanone of formula III, but this method generally offers no advantages over the other procedure.

Esters of formula I, for example alpha-cyano-3phenoxybenzyl 2,2,3,3-tetramethylcyclopropanecarboxylate, are valuable insecticides as disclosed in U.S. Pat. No. 3,835,176.

The Examples further illustrate the invention.

EXAMPLES I–VII

A 50-ml round-buttomed flask provided with a magnetic stirrer was charged with 10 mmol of 3-phenoxybenzaldehyde, 10 mmol of 2-chloro-3,3,4,4-tetramethylcyclobutanone, 12 mmol of a cyanide, 20 ml of n-heptane and water. The reaction mixture was stirred vigorously and analyzed by gas-liquid chromatography to determine the yield of the alpha-cyano-3-phenoxybenzyl 2,2,3,3-tetramethylcyclopropanecarboxylate formed. Seven experiments were conducted in this manner, except where indicated otherwise. The cyanide used, the amount of water added, the reaction temperature and the time of stirring are stated in Table I. The starting amount of 12 mmol of KCN in Examples I, III and IV formed a 44%w aqueous solution, in Examples II and V a 28%w aqueous solution. The starting amount of 12 mmol of NaCN in Examples VI and VII formed a 37%w aqueous solution. Table I also presents the yield of the desired ester, calculated on starting 3-phenoxybenzaldehyde.

TABLE I

| Example No. | Cyanide | Water, ml. | Temperature, °C | Time, h. | Yield of ester, % |
|---|---|---|---|---|---|
| I | KCN | 1 | 65 | 6 | 91 |
| II | KCN | 2 | 65 | 6 | 81[1] |
| III | KCN | 1 | 93 | 3 | 79[1] |
| IV | KCN | 1 | 25 | 20 | 46 |
| V | KCN[2] | 2 | 65 | 8 | 81 |
| VI | NaCN | 1 | 65 | 20 | 55 |
| VII | NaCN | 1 | 25 | 24 | 42 |

[1] the 2-chloro-3,3,4,4-tetramethylcyclobutanone was fully converted; the conversion of 3-phenoxybenzaldehyde was 85%.
[2] the 2-chloro-3,3,4,4-tetramethylcyclobutanone was added to the reaction mixture over a period of 1¼ hours.

The reaction mixture of Example I was cooled to 25° C, 10 ml of water was added to dissolve precipitated potassium chloride, the water layer was separated, the heptane layer was washed with 10 ml of water, dried over anhydrous calcium chloride and the n-heptane was flashed off in a film evaporator to yield a pale yellow oil which, according to quantitative gas-liquid chromatography, contained the desired ester in an amount corresponding to a yield of 88%.

EXAMPLE VIII

The experiment of Example I was repeated, but this time with 20 ml of cyclohexane instead of 20 ml of n-heptane and the rection mixture was kept at reflux temperature (about 81° C). After 6 hours' stirring the yield of the desired ester was 45%.

EXAMPLES IX AND X

A 50ml round-buttomed flask provided with a magnetic stirrer was charged with 10 mmol of benzaldehyde, 10 mmol of 2-chloro-3,3,4,4-tetramethylcyclobutanone, 12 mmol of sodium cyanide, 20 ml of a solvent and 1 ml of water. The reaction mixture was stirred vigorously at a temperature of 23° C. Two experiments ware carried out in this manner. Table II states the solvents used and presents the yields of the alpha-cyanobenzyl 2,2,3,3-tetramethylcyclopropanecarboxylate formed.

TABLE II

| Example, No. | Solvent | Time, h | Yield of ester, % |
|---|---|---|---|
| IX | n-heptane | 2.5 | 29 |
|  |  | 19 | 57 |
|  |  | 43 | 67 |
| X | toluene | 17 | 15 |

EXAMPLES XI AND XII

A 50-ml round-bottomed flask provided with a magnetic stirrer was charged with 10 mmol of benzaldehyde, 10 mmol of 2-chloro-3,3,4,4-tetramethylcyclobutanone, 12 mmol of a cyanide, 20 ml of n-heptane and 1 ml of water. The rection mixture was stirred vigorously at a temperature of 70° C. Two experiments were carried out in this manner. Table III states the cyanides used and presents the yields of the alpha-cyanobenzyl 2,2,3,3-tetramethylcyclopropane-carboxylate formed.

Table III

| Example, No. | Cyanide | Time, h | Yield of ester % |
|---|---|---|---|
| XI | KCN | 2.5 | 72 |
|  |  | 22 | 81 |

Table III-continued

| Example, No. | Cyanide | Time, h | Yield of ester % |
|---|---|---|---|
| XII | NaCN | 20 | 61 |

EXAMPLE XIII

A mixture of 100 mmol of benzaldehyde, 100 mmol of sodium cyanide and 50 ml of N,N-dimethylformamide was stirred at a temperature of 80° C for 30 min. Then, an amount of 100 mmol of 2-chloro-3,3,4,4-tetramethylcyclobutanone was added over a period of 30 min and stiring was continued for six hours. At the end of this period the reactants were fully converted and alpha-cyanobenzyl 2,2,3,3-tetramethylcyclopropanecarboxylate was obtained in a yield of 65%.

EXAMPLES XIV

A mixture of 100 mmol of benzaldehyde, 100 mmol of sodium cyanide and 50 ml of diisobutyl ketone was stirred at a temperature of 60° C for 30 minutes. Then, an amount of 100 mmol of 2-chloro-3,3,4,4-tetramethylcyclobutanone was added over a period of 30 min and stirring was continued for 100 hours. The conversion of benzaldehyde was 75% and the yield of alpha-cyanobenzyl 2,2,3,3-tetramethylcyclopropanecarboxylate 52%, calculated on starting benzaldehyde.

We claim:

1. A process for the preparation of an ester of formula I

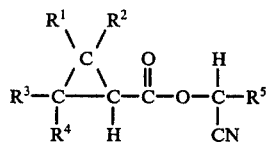
(I)

wherein $R^1$, $R^2$, $R^3$, and $R^4$ each represents an alkyl group containing from 1 to 6 carbon atoms, a cycloalkyl group containing from 3 to 6 carbon atoms, a phenyl group, an ethylenically unsaturated group containing from 2 to 4 carbon atoms, or a hydrogen atom, and $R^5$ represents a phenoxyphenyl group which comprises contacting (a) an aldehyde of formula II $R^5$—C(0)H  (II)

wherein $R^5$ has the same meaning as in formula I, (b) an alkali metal, alkaline earth metal or tetrahydrocarbylammonium salt of hydrocyanic acid, (c) a 2-halocyclobutanone of formula III

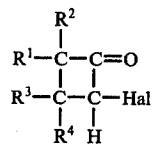
(III)

wherein $R^1$, $R^2$, $R^3$ and $R^4$ have the same meaning as in formula I and Hal represents a halogen atom, and (d) one or more aprotic solvents.

2. A process according to claim 1, in which the aprotic solvent is substantially immiscible with water, which is present as well.

3. A process according to claim 2, in which the substantially water-immiscible aprotic solvent comprises an alkane or a mixture of alkanes.

4. A process according to claim 3, in which the alkane is n-heptane.

5. A process according to claim 2, in which the amount of water is less than the amount required to obtain a 25%w aqueous solution with the starting amount of a water-soluble salt of hydrocyanic acid, but sufficiently large to dissolve all of this cyanide at the temperature at which the process is conducted.

6. A process according to claim 1, which is conducted at a temperature in the range of from 50° to 80° C.

7. A process according to claim 1, in which the aldehyde of formula II and the 2-halocyclobutanone of formula III are used in equimolar amounts.

8. A process according to claim 1, in which the molar ratio of the salt of hydrocyanic acid to aldehyde of formula II is in the range of from 1.0 to 1.5.

9. A process according to claim 1, in which the salt of hydrocyanic acid is an alkali-metal cyanide.

10. A process according to claim 9, in which the alkali-metal cyanide is potassium cyanide.

11. A process according to claim 1, in which $R^1$, $R^2$, $R^3$ and $R^4$ in formula III each represents an alkyl group having one to six carbon atoms.

12. A process according to claim 11, in which $R^1$, $R^2$, $R^3$ and $R^4$ each represents a methyl group.

13. A process according to claim 1, in which Hal in formula III represents a chlorine or bromine atom.

* * * * *